United States Patent [19]

Studt et al.

[11] Patent Number: 4,704,401
[45] Date of Patent: * Nov. 3, 1987

[54] SUBSTITUTED PHENYL AMIDINOUREAS

[75] Inventors: William L. Studt, Harleysville; Richard L. Riley, North Wales; George H. Douglas, Malvern, all of Pa.

[73] Assignee: Rorer Pharmaceutical Corporation, Fort Washington, Pa.

[*] Notice: The portion of the term of this patent subsequent to Dec. 11, 2001 has been disclaimed.

[21] Appl. No.: 678,639

[22] Filed: Dec. 6, 1984

Related U.S. Application Data

[63] Continuation of Ser. No. 280,786, Jul. 6, 1981, Pat. No. 4,487,779.

[51] Int. Cl.$^4$ .................... C07C 127/19; A61K 31/17
[52] U.S. Cl. ..................... 514/456; 514/464; 514/465; 514/596; 514/597; 514/598; 564/48; 564/49; 564/50; 564/51; 564/52; 564/53; 564/54; 549/229; 549/362; 549/439
[58] Field of Search ............... 514/598, 456, 464, 465, 514/596, 597; 564/48, 49, 50, 51, 52, 53, 54; 549/229, 439, 362

[56] References Cited

U.S. PATENT DOCUMENTS 4,060,635 11/1977 Diamond .............................. 514/598
4,150,154 4/1979 Diamond .............................. 514/598

OTHER PUBLICATIONS

Douglas, Arzneim-Forsch-Drug Res., 28-2 (8A), 1435 (1978).

Primary Examiner—Robert Gersil
Attorney, Agent, or Firm—James A. Nicholson; Alexis Barron; Martin F. Savitzky

[57] ABSTRACT

This invention relates to a method of lowering blood pressure in humans and mammals using 2,6-disubstituted phenyl amidinoureas in which the phenyl ring is additionally substituted by a hydroxy, alkoxy, aralkoxy, alkenyloxy, alkynyloxy, haloacyloxy, or acyloxy group and to novel 2,6-disubstituted phenyl amidinoureas which possess pharmaceutical properties, including blood pressure lowering activity.

5 Claims, No Drawings

SUBSTITUTED PHENYL AMIDINOUREAS

This is a continuation of co-pending application Ser. No. 280,786 filed on July 6, 1981, now U.S. Pat. No. 4,487,779.

FIELD OF THE INVENTION

This invention relates to certain substituted phenyl amidinoureas which exhibit blood pressure lowering activity, as well as other pharmaceutical properties.

REPORTED DEVELOPMENTS

Amidines and related compounds are known to exhibit antihypertensive properties as centrally acting antihypertensive agents.

Certain amidinoureas have been described as possessing blood pressure lowering effects in recently-issued patents, such as U.S. Pat. No. 4,088,785 which discloses amidinoureas in which an amidino nitrogen is phenyl substituted. Such amidinoureas are described as having antihypertensive effects in tests using the spontaneously hypertensive rat (Tabei et al, *Clin. Pharm. and Therap.* 11: 269–274, 1970). In addition, U.S. Pat. Nos. 4,117,165, 4,183,956 and 4,219,567 disclose antihypertensive activity for amidinoureas in which a urea nitrogen is substituted with a 2,6-disubstituted phenyl group and in which the amidino nitrogens are unsubstituted. In particular, these patents disclose that tests done according to the method of de Champlain et al, *Circulation Research*, xxii: 479 (1968), indicate antihypertensive properties for these compounds.

The antihypertensive activity of certain para-alkoxy-substituted phenyl derivatives of these compounds is reported in U.S. Pat. No. 4,216,230. This patent neither discloses the degree of effectiveness of these compounds, nor the tests by which their antihypertensive activity was evaluated.

The efficacy of the phenyl amidinourea compounds have been found to vary in different test subjects while the antihypertensive mechanism and active metabolites responsible for their blood pressure lowering effect have not been reported. An example of this unpredictability is disclosed in a monogram appearing in *Arzneimittel Forschung* 28 (II), 1433–1480 (1978). At page 1463 of this monogram, it is disclosed, that 1-(2'6-dimethylphenyl)-3-methylamidinourea (also known as lidamidine) has little or no effect on blood pressure over a dose range of 0.1 to 1.0 mg/kg administered intravenously. However, later investigations, as disclosed in copending U.S. patent application Ser. No. 26,161, filed Apr. 2, 1979, and assigned to the assignee of the present application, showed that this compound has a dose-related effect on blood pressure in humans following its administration in multiple daily doses.

The present invention relates to certain 2,6-disubstituted phenyl amidinoureas which possess surprising blood pressure lowering effects in humans and animals, including for example, a blood pressure lowering effect which may be induced relatively quickly after administration.

SUMMARY OF THE INVENTION

This invention relates to a method of lowering blood pressure in mammalian species which comprises administering to a patient, an effective blood pressure lowering amount of a compound of Formula I

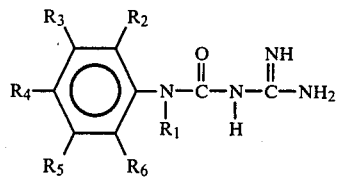

wherein:
$R_1$ is hydrogen or lower alkyl;
$R_2$ and $R_6$ may be the same or different and are alkyl, halo, alkoxy, nitro, haloalkyl, or alkylsulfonyl;
$R_3$, $R_4$ and $R_5$ may be the same or different and are hydrogen, hydroxy, alkoxy, aralkoxy, alkenyloxy, alkynyloxy, haloacyloxy, or acyloxy, provided that when $R_4$ is alkoxy then at least one of $R_3$ and $R_5$ is other than hydrogen; or
$R_3$ and $R_4$ together may be carbonyldioxy, methylenedioxy, or ethylenedioxy and form a 5 or 6 membered heterocyclic ring; provided further that at least one of $R_3$, $R_4$ and $R_5$ is other than hydrogen;
and the non-toxic pharmaceutically acceptable salts thereof.

Novel compounds of the present invention and possessing blood pressure lowering activity are also defined by Formula I.

Preferred compounds within the scope of Formula I are described below and are those compounds wherein the meta position of the phenyl group is substituted.

A particular advantage of this invention, among others, is the ability of compounds according to Formula I to induce a relatively fast blood pressure reduction in mammalian species.

Another advantage of this invention is that certain compounds according to Formula I, which have particular meta and/or para substituents on the phenyl group, possess selective blood pressure lowering activity in mammalian species, which activity is dependent on the method of its administration.

DETAILED DESCRIPTION OF THE INVENTION

A preferred class of compounds of this invention according to Formula I above include those where:
$R_1$ is hydrogen;
$R_2$ and $R_6$ are the same or different and are lower alkyl, lower alkoxy or halo;
and at least one of $R_3$, $R_4$ and $R_5$ are hydroxy, arloweralkoxy, lower alkyl acyloxy, lower alkoxy, lower alkenyl, or lower alkynyl;
provided that when $R_4$ is lower alkoxy, then at least one of $R_3$ or $R_5$ is other than hydrogen;
and the pharmaceutically acceptable salts thereof.

A more preferred class of these compounds is where:
$R_1$ is hydrogen:
$R_2$ and $R_6$ are lower alkyl, lower alkoxy or halo; and at least one of $R_3$ and $R_5$ is hydroxy, lower alkoxy, arloweralkoxy, or lower alkyl acyloxy.

Another preferred class of these compounds is where:
at least one of $R_3$, $R_4$ and $R_5$ is hydroxy.

The preferred embodiments of this invention include the subgroups in which the $R_1$, $R_2$ and $R_6$ substitutions are the preferred substitutions noted above and where:
$R_4$ is hydroxy, benzyloxy, 2-phenethoxy, or acetoxy, when $R_3$ and $R_5$ are each hydrogen;

$R_3$ is hydroxy, or lower alkoxy when $R_4$ and $R_5$ are each hydrogen;

$R_5$ is hydroxy or lower alkoxy when $R_3$ and $R_4$ are each hydrogen;

$R_3$ and $R_4$ are hydroxy, lower alkoxy, arloweralkoxy, or lower alkylacyloxy, when $R_4$ is hydrogen;

$R_3$ and $R_5$ are hydroxy, lower alkoxy, arloweralkoxy or lower alkylacyloxy; when $R_4$ is hydrogen; and all of $R_3$, $R_4$ and $R_5$ are hydroxy or lower alkoxy.

An embodiment of this invention, of particular interest, comprises a class of compounds of Formula I where $R_3$ and $R_4$ together form a cyclic carbonyldioxy or dioxyalkylene group such as shown in Formula II or III.

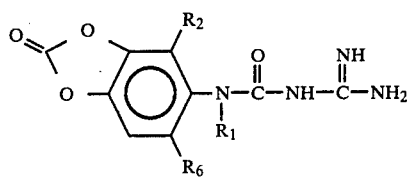

II

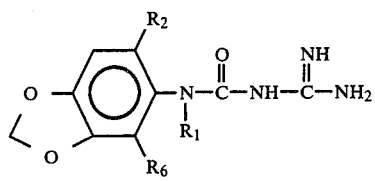

III

It is know that certain compounds of Formula I can exist in enolized or tautomeric forms or may be obtained as hydrates or in different polymorphic forms. One form may predominated over another depending upon the degree and locaton of substitution and, in solution, on the nature of the solvent. The rates of conversion of one tautomer to another will depend upon the nature of the solvent, the degree of hydrogen bonding permitted, the temperature and possibly other factors (such as pH, trace impurities and the like).

To illustrate what is meant by this, a number of likely structures are here shown for just one of the compounds in this invention.

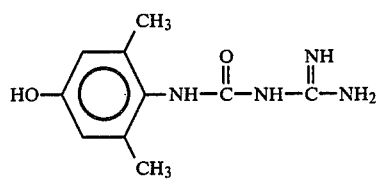

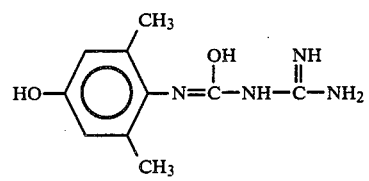

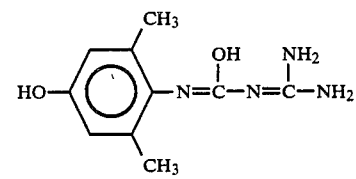

-continued

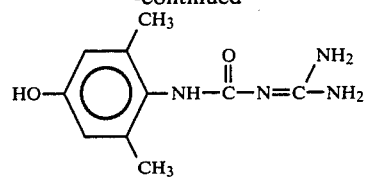

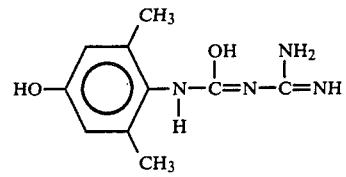

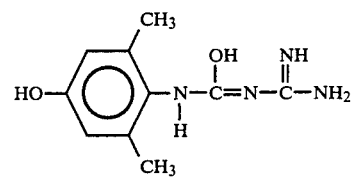

Of course, other types of structures are possible such as those with hydrogen bonding.

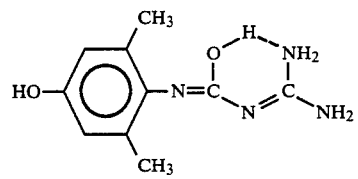

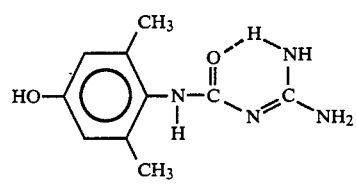

The structures given above are representative of this kind of phenomenon and are encompassed within the scope of this invention. It is predictable that, in physiological conditions, any one or all of these structures may exist or even predominate at the sites at which these molecules operate.

It is understood that the designations of the amidinoureas suitable for use in the practice of this invention are intended to include the compounds specifically named or shown by structure along with the alternative or transient states where such exist. It is also intended to include the pharmaceutically acceptable salts of the amidinoureas designated by Formula I. Such salts include the nontoxic addition salts as well as other salts, for example, quarternary ammonium salts.

It is generally accepted in the pharmacological arts that nontoxic acid addition salts of pharmacologically active amine compounds may be readily prepared from their free bases, without loss of activity. The salts merely provide a convenient solubility factor. The amidinoureas of this invention may be readily converted to their nontoxic acid addition salts by customary methods in the art. The nontoxic salts of this invention are formed from acids which are pharmacologically acceptable in the intended dosages. The nontoxic salts may be prepared from inorganic acids, and organic acids, including higher fatty acids, higher molecular weight acids, etc. Exemplary acids are hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

The nomenclature applied to the compounds of this invention is as follows:

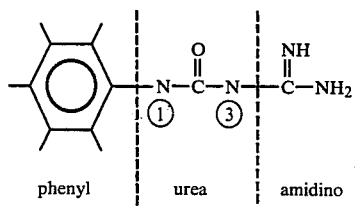

phenyl | urea | amidino

As employed above and throughout the disclosure, the following terms, unless otherwise indicated, shall be understood to have the following meanings.

"Alkyl" means a saturated aliphatic hydrocarbon which may be either straight- or branched-chain. Alkyl groups which have no more than about 12 carbon atoms are preferred and may be methyl, ethyl and structural isomers of propyl, butyl, pentyl, hexyl, heptyl, octyl, nonyl, decyl, undecyl and dodecyl. Also included are the cycloalkyl groups such as cyclopropyl, cyclopentyl, cyclohexyl, etc., and the cycloalkylakyl groups such as cyclopropylmethyl and the like.

"Lower alkyl" means an alkyl group as above, having 1 to 6 carbon atoms. Suitable lower alkyl groups are methyl, ethyl, n-propyl, isopropyl, butyl, isobutyl, sec-butyl, tert-butyl, n-pentyl, isopentyl and neopentyl.

The terms "halo" and "halogen" include all four halogens, namely, fluorine, chlorine, bromine and iodine. The halo alkyls include groups having more than one halo substituent which may be the same or different, such as trifluoromethyl, 1-chloro-2-bromo-ethyl, etc.

"Aryl" means phenyl or phenyl in which one or more of the phenyl hydrogens has been replaced by the same or different substituents selected from the group consisting of halo, lower alkyl, halo-lower alkyl, nitro, amino, lower alkanoyl, hydroxy, lower hydroxy, phenyl-lower alkoxy, lower alkanoyl, cyano, halo-lower alkoxy, and lower alkyl sulfonyl.

"Alkoxy" is intended to include hydroxy alkyl groups. Preferred lower alkyl groups such as methoxy, ethoxy, n-propoxy, i-propoxy, and the like.

"Aralkoxy" means an alkoxy group as above substituted with an aryl group. Preferred aralkoxy groups are arloweralkoxy groups such as, benzyloxy, 2-phenethoxy, etc.

The preferred "halo lower alkyl" group is trifluoromethyl.

The preferred "halo lower alkoxy" group is trifluoromethoxy.

The compounds of this invention may be prepared by the following general synthesis.

Condensation of a substituted phenyl isocyanate (prepared from an aniline and phosgene in the customary manner) with guanidine results in a substituted phenyl-3-amidinourea. The reaction is carried out in a polar media using solvents such as alcohol, tetrahydrofuran, etc. It is convenient to carry out the reaction by preparing the isocyanate in the reaction media and then forming guanidine in situ by hydrolyzing guanidine carbonate with base. Condensation of the isocyanate takes place when the guanidine forms and the amidinourea compound results.

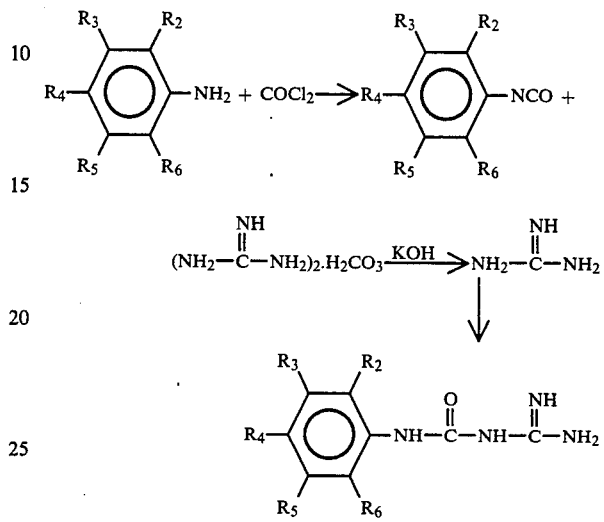

The amidinourea compounds may also be prepared by degradation of the corresponding biguanide. When a 1-substitutedphenylbiguanide compound is hydrolyzed in acid at elevated temperature, then the resultant product is 1-substituted phenyl-3-amidinourea. This reaction is preferably carried out using hydrochloric acid. The reaction time and reaction temperature depend on the particular biguanide used and the concentration of the acid present. In general, the more concentrated acids will not require high temperatures or long periods of reaction time.

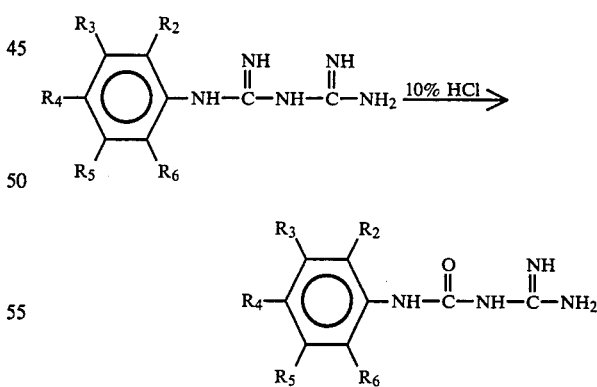

The introduction $R_1$ to $R_6$ substituents into the pheylamidinourea structure may be accomplished by choosing appropriately substituted starting materials. For example, when $R_1$ substitution is desired, the starting material can be an aniline having N-alkyl substitution. Reaction with phosgene results in the aniline acid chloride which is than reacted with the guanidine to prepare the amidinourea.

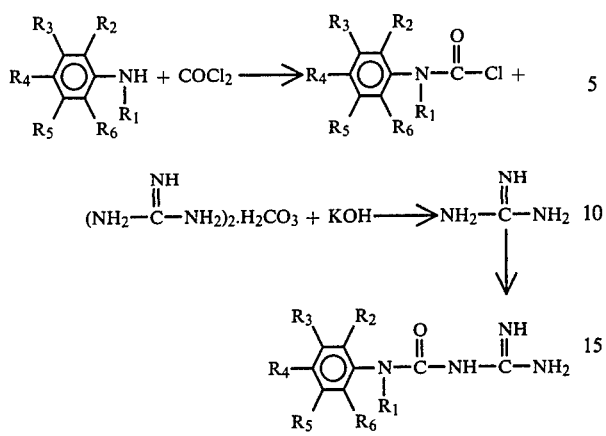

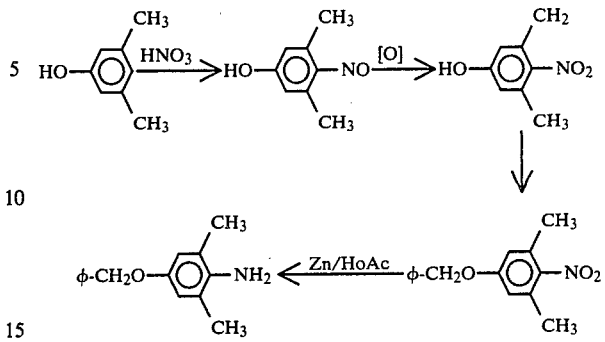

Substitution in the meta or para positions of the phenyl moiety may be accomplished either before or after the amidinoureas is formed by any means known to those skilled in the art including the use of an appropriate enzyme reagent, such as, a hydroxylase.

It is preferred that the starting aniline contain any substituent groups which may be desired in the amidinourea final product. The hydroxy groups may be in protected form, i.e., in the form of the corresponding acyloxy or aralkyloxy group. The acyloxy or aralkyloxy groups may be prepared by acylating the starting hydroxy aniline compound with an acyl halide or an anhydride in the presence of a base or by aralkylating with an aralkyl halide or sulfate while the amine function is protected in the customary manner. Hydrogenolysis or hydrolysis to the desired hydroxy compound may then take place after the formation of the amidinourea. Hydrogenolysis may be accomplished with a metal catalyst (Pd/C, Pt etc.) in a polar medium (ethanol, THF, etc.), sodium in liquid ammonia, etc. and hydrolysis of the acyl or aralkoxy compounds accomplished with aqueous acid. Thus, for example, the 3,4-dihydroxy-2,6-dimethylphenyl amidinourea compound may be prepared from the corresponding 3,4-dibenzyloxy-2,6-dimethylaniline.

The starting hydroxy or alkoxy anilines or protected hydroxy anilines are either known, or may be prepared by known techniques. For example, aryl compounds may be hydroxylated according to methods noted in "Compendium of Organic Synthetic Methods", Harrison and Harrison (John Wiley & Sons 1971) section 41, hereby incorporated by reference. See also, "Reagents for Organic Synthesis", Fieser and Fieser, Vol. 1 at page 474.

4-hydroxy-2,6-disubstituted anilines may be prepared starting from the 3,5-disubstituted phenol by forming the 4-nitroso phenol which is further oxidized to the 4-nitrophenol. The phenolic hydroxy group may then be masked by an appropriate protecting group and the nitro compound reduced to the desired aniline. The following schematic reaction sequence illustrates this general synthesis.

3-hydroxy-2,6-disubstituted anilines may be prepared as depicted in the following sequence starting from a 2,6-disubstituted nitrobenzene. Nitrating meta to the nitro substituent followed by selective reduction yields an amino group which is then converted to the desired hydroxy substituent.

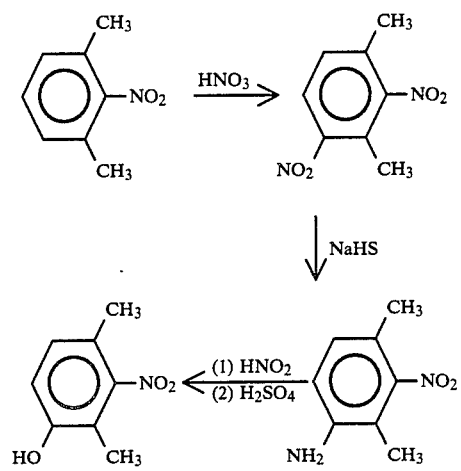

3,4-dihydroxy-2,6-disubstituted anilines may be prepared from a 3,4-methylenedioxy aniline by halogenating the 2 and 6 positions of the aniline and deprotecting the 3 and 4 positions. The aniline may be utilized in its protected form and deprotected after the amidinourea is formed.

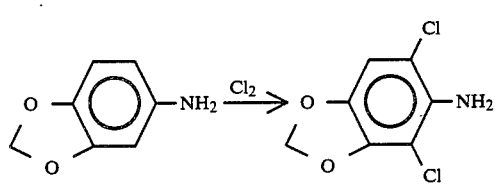

3,4-dibenzyloxy, or a 3,4-dimethyoxy aniline may also be utilized and 2,6-dimethyl substitution effected according to the following general scheme.

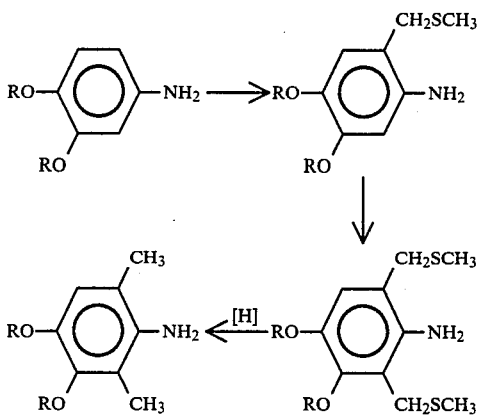

The preparation of other 3-,4- and 5- substituted anilines will be readily apparent to those skilled in the art.

Phenyl substitution may also be carried out at other stages of synthesis depending on the substituents present and the substituents desired. Various combinations of the foregoing reactions can be determined by one skilled in the art in order that the desired product results. Thus, a phenylamidinourea may be halogenated or nitrated as above, etc.

The biguanide starting materials are also either known, or may be prepared by known procedures, such as, the following general synthesis.

Condensation of cyanoguanide and a protected hydroxylated aniline in the presence of an equimolar amount of a mineral acid results in the corresponding phenylbiguanide.

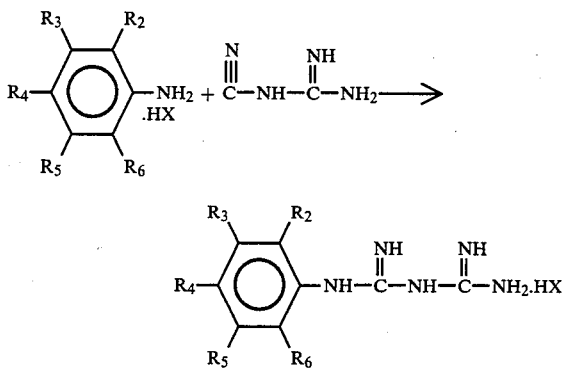

This reaction is preferably carried out on the aniline salt either in a polar media or neat and using increased temperatures. The appropriately substituted product may be prepared by the reactions above when these are also carried out on the biguanide.

The following are detailed examples which show the preparation of the compounds of this invention.

EXAMPLE I

The preparation of
1-(2,6-dimethyl-4-hydroxyphenyl)-3-amidinourea

Step 1

3,5-dimethyl-4-nitrosophenol 750 ml of concentrated HCl are added to a solution of 3,5-dimethyl phenol (80.6 g) in 750 ml of 95% ethyl alcohol. The mixture is cooled to 0° C. in an ice/methanol bath. While maintaining the temperature of the reaction mixture below 5° C., a solution of $NaNO_2$ (69.0 g) in 150 ml of $H_2O$ is added dropwise to the reaction mixture. The mixture is stirred at 0° C. for more than an hour and then poured into 9 liters of water. The aqueous mixture is filtered to give a yellow solid which is recrystallized from hot methanol and filtered to give 71.45 grams of a yellow solid, M.P. 180°–181° C. (dec).

Step 2

3,5-dimethyl-4-nitrophenol

A mixture of 3,5-dimethyl-4-nitrosophenol (70.63 g), and $(NH_4)_6Mo_7O_{24}.4H_2O$ (2.83 g) in 770 ml of glacial acetic acid is warmed on a steam bath. 30% $H_2O_2$ (84 ml) is added to the mixture in 10 ml portions until an exothermic reaction is observed. The reaction mixture is then stirred and the remainder of the $H_2O_2$ solution added in small portions. The reaction mixture is heated and stirred until a clear dark red solution results. A yellow-orange solid precipitated from the solution after stirring for another 20–30 minutes. The reaction mixture is stirred overnight and filtered to give a small amount of a yellow solid and a clear dark red filtrate. The red filtrate is concentrated in vacuo and partitioned between $H_2O$ and ether. The aqueous layer is washed with ether and the combined ether extracts washed with 10% sodium carbonate until the aqueous layer becomes basic. The ether extract is dried, filtered, and concentrated in vacuo to a yellow-orange solid. The solid is dissolved in hot toluene, filtered, concentrated and allowed to cool overnight. After cooling in an ice bath, the mixture is filtered to give 49.5 grams of a yellow-green solid identified as 3,5-dimethyl-4-nitrophenol, M.P. 106°–108° C.

Step 3

5-benzyloxy-2-nitro-meta-xylene

A mixture of 3,5-dimethyl-4-nitrophenol (17.6 g), benzyl chloride (20.0 g) and anhydrous $K_2CO_3$ (13.2 g) in acetone (100 ml) is stirred under reflux for 22 hours. The reaction mixture is filtered and the precipitate washed with acetone. The acetone extract is concentrated in vacuo and the residue short path distilled (160°–170° C.; 50μ) to give 22.9 grams of an orange liquid which crystallized on standing.

Step 4

4-benzyloxy-2,6-dimethylaniline

Zinc dust is added to a solution of 5-benzyloxy-2-nitro-m-xylene (22.9 g) in 250 ml of glacial acetic acid. The reaction mixture is stirred until the solution is colorless. The reaction mixture is cooled, filtered through celite to remove excess zinc and the filtrate diluted with $H_2O$ and cooled with ice. $NH_3$ is added to make the solution slightly alkaline followed by a small amount of sodium hydrosulfite. The product is filtered, dissolved in methylene chloride, dried and concentrated to give 18.3 grams of a tan solid.

Step 5

4-benzyloxy-2,6-dimethylphenyl isocyanate

Excess $COCl_2$ is bubbled into a solution of 4-benzyloxy-2,6-dimethylaniline (18.3 g) in toluene (250 ml). The reaction mixture is brought to reflux and approximately 200 ml of toluene are distilled off. The reaction mixture is concentrated in vacuo to give a brown solid which is vacuum distilled (T=170°–185° C.) to give 17 grams of the desired product.

Step 6

1-(4-benzyloxy-2,6-dimethylphenyl)-3-amidinourea hydrochloride

A 50% NaOH aqueous solution (8.0 g) is added to a suspension of guanidine carbonate (9.0 g) in 200 ml of THF. The mixture is stirred for one hour, after which 15.0 grams of anhydrous $Na_2SO_4$ are added and the mixture stirred an additional hour. A solution of 4-benzyloxy-2,6-dimethylphenyl isocyanate (12.7 g) in 100 ml HTF is added to the mixture over a period of 4 hours. The reaction mixture is allowed to stand overnight, filtered, and the filtrate concentrated under vacuum. The filtrate is partitioned between $H_2O$ and $CHCl_3$. The two layers are filtered to remove insoluble materials and then separated. The aqueous layer is extracted with $CHCl_3$ and the combined $CHCl_3$ extracts dried and concentrated under vacuo to give a tan solid. This solid is dissolved in methanol and acidified with HCl/methanol. Methanol is removed under vacuo to give a solid which is crystallized from methanol/acetonitrile to give after filtering and vacuum drying 9.8 grams of the desired amidinourea hydrochloride, M.P. 181°–183° C.

Step 7

1-(4-hydroxy-2,6-dimethylphenyl)-3-amidinourea hydrochloride

A mixture of 1-(4-benzyloxy-2,6-dimethylphenyl)-3-amidinourea hydrochloride (7.0 g), methanolic HCl (50 ml), 5% Pd/C (1.0 g) and 150 ml of absolute ethanol are shaken under an atmosphere of $H_2$ (50 psi) until the uptake of hydrogen ceases. The mixture is filtered through a pad of Celite and the pad washed well with methanol. The filtrate is concentrated under vacuo and the residue crystallized from methanol/acetonitrile to give, after filtering and vacuum drying, 4.7 grams of an off-white solid, M.P. 204°–206° C. Recrystallization from methanol/acetonitrile gave, after filtering and vacuum drying, 2.3 grams, M.P. 208°–210° C. of the hydrochloride salt.

EXAMPLE II

The preparation of 1-(3-hydroxy-2,6-dimethylphenyl)-3-amidinourea

Step 1

1,3-dimethyl-2,4-dinitrobenzene 1,3-dimethyl-2-nitrobenzene (151.2 g) is dissolved in 500 ml of $CH_2Cl_2$ and cooled to below 0° C. in a methanol ice bath. Sulfuric acid (200 ml) is added dropwise, maintaining a temperature at below 0° C. After the sulfuric acid addition is complete, fuming nitric acid (86 ml) is added dropwise at a rate which maintains the temperature between −5° to −2° C. After the addition is complete, the mixture is stirred at −3° to −5° C. for 2 hours. 200 ml of water are carefully added to the aqueous acidic layer and, after cooling to RT, the mixture is extracted with 600 ml of $CH_2Cl_2$. The extracts are combined and washed with 600 ml of $H_2O$, saturated NaCl solution and dried overnight. The mixture is filtered and the filtrate concentrated to give 192.2 grams of a yellow solid, M.P. 81°–83° C.

Step 2

2,4-dimethyl-3-nitro aniline (a) Preparation of sodium sulfide reducing agent $Na_2S$ is dissolved in 750 ml of $H_2O$ and cooled in an ice water bath. Sodium bicarbonate is added at a rate so that the temperature does not exceed 15° C. The reaction mixture is stirred after the addition is complete and 800 ml of methanol are added so that the temperature does not exceed 25° C. and stirred for 15 min. The reaction mixture is filtered.

(b) Reduction of nitro aniline

The filtrate from above is added to a solution of 128.75 grams of nitroaniline in approximately one liter of methanol and heated to reflux for one and one half hours and stirred at room temperature overnight. The mixture is refluxed until all starting material has been consumed. Additional reducing agent is added if needed. The reaction mixture is filtered and the filtrate concentrated. One liter of water is added, stirred, filtered and the precipitate is washed with water and dried to give 105.6 grams of a yellow solid, M.P. 78°–79° C.

Step 3

2,4-dimethyl-3-nitrophenol 2,4-dimethyl-3-nitroaniline (105.6 g) is added to a reaction mixture containing 300 ml of $H_2SO_4$ and 300 ml of $H_2O$. The reaction mixture is stirred at a temperature of 105°–108° C. for one half hour and then cooled to 0° C. A solution of sodium nitrite (52.6 g) in $H_2O$ (124 ml) is added dropwise. After addition is complete the reaction mixture is poured into a 50% aqueous $H_2SO_4$ solution (2,000 ml) and refluxed for one and one half hours. The reaction mixture is cooled over the weekend to ambient temperature, and filtered leaving a yellow and black solid which is washed with $H_2O$, dried and boiled with hexanes (8 l). The hexane extract is concentrated and filtered to obtain 65.4 grams of a yellow solid, M.P. 99°–101° C.

Step 4

4-benzyloxy-2-nitro-m-xylene 56.6 grams of 2,4-dimethyl-3-nitrophenol, 64.5 grams of benzyl chloride and 74.6 grams of anhydrous $K_2CO_3$ are stirred under reflux for 24 hours. The reaction mixture is filtered through a pad of Celite and the Celite washed with acetone. The filtrate is concentrated in vacuo and the residue vacuum distilled to give 83.9 grams of the benzyloxy xylene (B.P. 150–°160° C., 5 μ). The material solidified on standing.

Step 5

3-benzyloxy-2,6-dimethylaniline

Zinc dust is added in portions to a solution of 4-benzyloxy-2-nitro-m-xylene (83.8 g) in glacial acetic acid (715 ml). Addition is complete when the exothermic reaction subsides. The reaction mixture is filtered through Celite and the pad washed with acetic acid. The filtrate is concentrated in vacuo and the residue diluted with $H_2O$ and made basic with ammonium hydroxide, and extracted with chloroform. The combined organic extracts are dried and concentrated in vacuo to give the desired aniline in quantitative crude yield.

Step 6

3-benzyloxy-2,6-dimethylphenyl isocyanate

Excess phosgene is bubbled into a solution of 3-benzyloxy-2,6-xylidene (74.9 g) in 750 ml of toluene. The reaction mixture is heated at reflux and, after the reaction mixture clarified, 500 ml of toluene are removed by distillation at atmospheric pressure. The remaining toluene is removed under vacuo. The residue is distilled under vacuo to give an orange-brown liquid (B.P. 160°–175° C. 50μ).

Step 7

1-(3-benzyloxy-2,6-dimethylphenyl)-3-amidinourea hydrochloride 25.3 grams of 3-benzyloxy-2,6-dimethylphenol isocyanate in 200 ml of THF are added dropwise to a suspension of 18.0 grams of guanidine carbonate in THF (400 ml) to which 16 grams of a 50% aqueous sodium hydroxide solution has been added. The addition takes 6 hours after which the reaction mixture is allowed to stir overnight. The reaction mixture is filtered and the filtrate concentrated in vacuo. The residue is partitioned between $H_2O$ and $CH_2Cl_2$ and the layers separated. The aqueous layer is extracted with methylene chloride and the combined methylene chloride extracts dried, filtered, and the filtrate acidified with HCl in methanol. The filtrates are concentrated in vacuo to give a foam which is recrystallized from acetonitrile/ethyl acetate. The resultant solid is recrystallized from acetonitrile and dried in vacuo to give 27.9 grams of a tan solid, M.P. 168°–169° C.

Step 8

1-(2,6-dimethyl-3-hydroxy-phenyl)-3-amidinourea hydrochloride

A mixture of 1-(3-benzyloxy-2,6-dimethylphenyl)-3-amidinourea hydrochloride (17.4 g) and 5% Pd/C (1.0 g) in absolute ethanol (200 ml) containing 50 ml of methanolic HCl is shaken under an atmosphere of $H_2$ (50 psi) for 45 minutes. The reaction mixture is filtered through Celite and the Celite washed with methanol. The filtrate is concentrated in vacuo and the foam taken up in acetonitrile. The acetonitrile solution is concentrated in vacuo and the residue crystallized from methanol/acetonitrile to give, after filtering and vacuum drying, 10.1 grams of the 3-hydroxy phenyl amidinourea hydrochloride salt , M.P. 207°–208° C. (dec).

EXAMPLE III

Preparation of 1-(2,6-dimethyl-3-methoxyphenyl)-3-amidinourea hydrochloride

Step 1

2,4-dimethyl-3-nitroanisole

A mixture of 32.12 grams of 2,4-dimethyl-3-nitrophenol, 35.78 grams of methyltosylate and 28.5 grams of anhydrous $K_2CO_3$ in 200 ml of acetone is heated to reflux for 12 hours. The reaction mixture is filtered leaving a tan solid. The filtrate is concentrated in vacuo. The concentrated filtrate is taken up in ethyl acetate and extracted with 10% aqueous sodium hydroxide solution and saturated aqueous sodium chloride. The remaining ethyl acetate layer is dried, filtered and concentrated in vacuo to give a dark oil which is distilled (T=80°–87° C./50μ) to give 30.95 grams of a yellow solid which is recrystallized from absolute ethanol, M.P. 53°–55° C.

Step 2

2,6-dimethyl-3-methoxyaniline hydrochloride 30.0 grams of 2,4-dimethyl-3-nitroanisole and 44.45 grams of zinc metal dust are refluxed in 100 ml of toluene. 150 ml of a glacial acetic acid are cautiously added dropwise to the reaction mixture. The reaction mixture is refluxed for two and one-half hours after the addition of glacial acetic acid is complete, and allowed to sit over the weekend. The reaction mixture is filtered and the filtrate concentrated in vacuo. The resulting dark oil is taken up in 400 ml of methylene chloride and washed with 50 ml of concentrated ammonium hydroxide and 800 ml of water. The methylene chloride solution is dried, filtered and concentrated in vacuo to give a dark oil. The oil is dissolved in ether and the ether solution acidified with HCl/ether. The methoxy aniline hydrochloride salt is obtained as 27.4 grams of a purple precipitate, M.P. 216°–221° C.

Step 3

2,6-dimethyl-3-methoxyphenyl isocyanate 29.68 grams of phosgene gas are bubbled into a stirred mixture of 26.3 grams of 2,6-dimethyl-3-methoxyaniline hydrochloride in 450 ml of chlorobenzene. The reaction mixture is refluxed for one hour after bubbling in the 20% NaOH trap ceases. The reaction mixture is concentrated in vacuo to a dark oil and the dark oil distilled (70°–77° C./50μ) to give 19.46 grams of the isocyanate as a yellow liquid.

Step 4

1-(2,6-dimethyl-3-methoxyphenyl)-3-amidinourea hydrochloride 6.4 grams of a 50% aqueous sodium hydroxide solution are added to a stirred mixture of 7.21 grams of guanidine carbonate in 300 ml of THF. The mixture is stirred for one-half hour and 10 grams of $Na_2SO_4$ added and the mixture stirred for an additional half hour. A solution of 7.09 grams of the 3-methoxyphenyl isocyanate in 100 ml of THF is slowly added dropwise to the reaction mixture. After the isocyanate addition is complete, the reaction mixture is filtered and concentrated in vacuo to give a yellow oil. The oil is partitioned between $H_2O$ and ether. A light yellow solid is suspended between the layer which is collected and air dried. The $H_2O$ layer is repeatedly extracted with ether and methylene chloride. The organic extracts are combined, dried and concentrated in vacuo to yield a yellow oil which is dissolved in methanol. HCl in methanol is added to this mixture, and the resultant clear solution is filtered and concentrated in vacuo. 50 ml of ethyl acetate is added to the oil, heated and stirred to give 8.89 grams of a white solid, M.P. 196°–198° C. The white solid was recrystallized from hot acetonitrile, M.P. 197°–199.5° C.

EXAMPLE IV

Preparation of
1-(2,6-dichloro-3-hydroxyphenyl)-3-amidinourea
hydrochloride monohydrate

Step 1

2,6-Dichloro- 3-hydroxybenzoic acid m-Hydroxybenzoic acid (337 g) is suspended in glacial acetic acid (1700 ml) and chlorine gas (346 g) bubbled into the suspension over a period of two hours forty-five minutes while maintaining the temperature of the suspension at 18°–20° C. The reaction mixture is stirred for an additional thirty minutes, water (100 ml) added, and the mixture evaporated in vacuo to a light green syrup. The light green syrup is dissolved in boiling water (3300 ml), filtered while hot, and rinsed with hot water, resulting in a clear solution (about 3500 ml), which is stirred overnight at R.T. The resulting suspension is filtered, the precipitate washed ($H_2O$ 1 liter) and suspended in 1 liter $H_2O$. The suspension is filtered, washed (500 ml $H_2O$), and dried on a Buchner funnel for two hours. The precipitate is dissolved in 3.5 liters of hot $H_2O$, filtered while hot, and allowed to cool, with stirring to R.T. (about three hours). The suspension is filtered and the solid washed (2 1 $H_2O$) and dried on a Buchner overnight, giving 271.9 g of a white crystalline solid, MP 119°–121° C.

Step 2

3-Benzyloxy-2,6-dichlorobenzoic acid 271.6 g of 2,6-dichloro-3-hydroxybenzoic acid are dissolved in ethanol (2 1). Aqueous sodium hydroxide (242 g of 50% aqueous NaOH solution in 550 ml $H_2O$) is added to the benzoic acid solution, followed by the addition of benzyl chloride (368 g). The reaction mixture is heated to reflux with stirring, and after one hour, additional sodium hydroxide solution (45 g of a 50% aqueous NaOH) and benzyl chloride (30 g) are added. After one hour twenty-five minutes, another 20 g of 50% sodium hydroxide solution are added. After twenty minutes, the reaction mixture is cooled and evaporated to remove ethanol. The mixture is then partitioned between diethylether (2 1) and 5% aqueous sodium hydroxide (2 1). The layers are separated and the aqueous solution washed with diethylether. The aqueous extract is cooled in an ice bath and acidified just short of neutral with conc. HCl. Diethylether (2 1) is added and the solution made strongly acidic. The two layers are stirred for fifteen minutes and separated. The aqueous layer is washed with diethylether and the combined ether layers washed with $H_2O$, saturated sodium chloride solution, and dried over $Na_2SO_4$. The ether is filtered and the filtrate evaporated in vacuo to a light yellow oil (338.2 g). 500 ml of toluene are added to the oil and partially evaporated, resulting in a precipitate. The suspension is allowed to stand and used without further treatment for the further reactions. The toluene suspension contains a large amount of heavy crystalline precipitate.

Step 3

3-Benzyloxy-2,6-dichlorobenzamide

The toluene suspension, from Step 2 above, is combined with an additional 2 liters of toluene and stirred. Pyridine (1.5 ml) is added, followed by the addition of thionyl chloride (271 g). The reaction mixture is heated to reflux for three and one-half hours, allowed to cool, and evaporated in vacuo. The amber oil residue is dissolved in 1 liter of toluene and evaporated to a light brown oil. 100 ml of anhydrous diethylether are added to the oil and allowed to stand overnight, resulting in the precipitation of a crystalline solid. 600 ml anhydrous diethylether are added, giving a solution containing a fluffy undissolved material. The solution is filtered, giving a slightly cloudy solution. 1.1 liters of concentrated ammonium hydroxide are added to the stirred solution over a period of thirty minutes while maintaining the temperature between 5° and 10° C. in an ice bath. After addition is complete, the mixture is stirred for an additional one hour. The reaction mixture is filtered and the solid washed with water (2 1). The moist solid is dissolved in boiling methanol (1200 ml) and filtered, rinsed with hot methanol (150 ml), and allowed to cool, with stirring, at R.T. for two hours, then in an ice bath for thirty minutes. The precipitate is filtered and the solid washed with 500 ml cold methanol, dried on a Buchner and allowed to air dry. The filtrate and wash are evaporated in vacuo to approximately 100 ml of a slurry. The first crop of crystals dried to 174.6 g of near-white crystals, MP 159.5°–161° C. The slurry was heated to boiling and allowed to cool, stirred at R.T., and then in an ice bath for two hours, filtered, the solid washed with methanol and dried to give 51 g of a chunky solid, MP 155°–158° C. The first and second crops of crystals are identical and are the desired benzamide.

Step 4

3-Benzyloxy-2,6-dichloroaniline 58 g of chlorine gas are bubbled into an aqueous sodium hydroxide solution (375 g of 50% aqueous NaOH in 2 1 of $H_2O$ and crushed ice) while cooling in an ice bath over a period of twenty-five minutes. After the addition is complete, the chlorine solution is stirred for five minutes and 3-benzyloxy-2,6-dichlorobenzamide (220.8 g) added over a period of five minutes. The reaction mixture is stirred in the ice bath for one and one-half hours. Another 280 ml of a 50% aqueous sodium hydroxide solution are added and the mixture heated to 80° C. over a period of one hour fifteen minutes. The reaction mixture is stirred at. 80°–85° C. for one hour, cooled to room temperature in an ice bath and stirred with 3 liters diethylether, giving a biphasic system with a large amount of dark solid. The solid is collected by filtration and washed with diethylether and dried overnight, giving 92.8 g of near-black crystals (starting amide). The ether solution is washed with water, saturated sodium chloride, dried and filtered. The ether filtrate is evaporated in vacuo to 120 g of a sticky brown solid which is triturated with ether (250 ml), filtered, and the filtrate acidified with ether/HCl. The resulting precipitate is collected, washed with ether and dried, giving 288 g of the HCl salt as a dark purple powder. The salt is partitioned between ether and 10% aqueous NaOH. The ether extract is dried and evaporated in vacuo to 23.4 g of the desired aniline.

Step 5

3-Benzyloxy- 2,6-dichlorophenylisocyanate

The aniline from Step 4 above is dissolved in 250 ml toluene and stirred while 20–30 ml of phosgene liquid is passed into the solution (as a gas) over a period of about five minutes. After addition is complete, the mixture is heated to reflux for three hours and the solvent allowed to distill off. When about one-half of the solvent has been removed, the mixture is allowed to cool and then evaporated in vacuo to give 26.8 g of a dark oil. The oil is distilled in vacuo using a short path column, collecting 16.5 g of a liquid which distills at a temperature of 170°–190° C./0.05 mm Hg and solidifies in the collecting flask. IR spectrum indicates the desired isocyanate.

Step 6

3-Benzyloxy-2,6-dichlorophenyl-3-amidinourea

Guanidine hydrochloride (7.8 g) is suspended in acetone (150 ml). A 50% aqueous sodium hydroxide solution (6.53 g) is added to the guanidine suspension. The mixture is stirred for one and one-half hours, after which 15 g anhydrous sodium sulfate are added and the reaction mixture stirred vigorously for an additional hour. The isocyanate obtained in Step 5 above (8.0 g) is dissolved and suspended in 50 ml acetone. This suspension is added to the reaction mixture over a period of one hour fifteen minutes. The reaction mixture is stirred overnight, filtered, and the filtrate evaporated in vacuo to a green oil. The green oil is triturated in 200 ml of $H_2O$ containing 5 drops of a 50% aqueous sodium hydroxide solution. The resulting suspension is stirred for three hours, filtered, and the solid washed with water and dried. After air drying overnight, there is obtained 12.9 g of a white powder which is dried in vacuo at 30°–35° C. for four hours, giving 9.47 g of white powder. The powder is dissolved in 50 ml of methanol. The methanol solution is filtered and the filtrate acidified with methanol/HCl. The acidified solution is evaporated in vacuo (30°–35° C.) to yield the hydrochloride salt as a light-colored oil, which is utilized without further treatment.

Step 7

2,6-Dichloro-3-hydroxyphenyl-amidinourea

The hydrochloride salt of Step 6 above is dissolved in a mixture of absolute ethanol (90 ml) and methanol/HCl (10 ml). 5% palladium on charcoal (0.90 g) is added to the solution which is stirred under hydrogen at atmospheric pressure. 585 ml of hydrogen are absorbed in 45 minutes. The mixture is filtered and the filtrate evaporated to a clear, colorless oil which is dissolved in 25 ml $H_2O$ and 25 ml conc. HCl. A gummy precipitate results. The gummy suspension is stirred and triturated for several hours, slowly forming a solid. After stirring for three hours, the mixture is cooled in an ice bath for thirty minutes, filtered, and the precipitate washed with 25 ml cold 18% HCL, about 5 ml acetonitrile, and then diethylether. The solid is dried on a Buchner and then at 40°–45° C. at 0.1 mm Hg for two hours. This resulted in 5.0 g of a white powder. The melting point of this compound occurred at two stages. The material first melted at approximately 124°–130° C., then stayed solid, melting at 201°–203° C. IR and elemental analysis indicated the desired amidinourea as the hydrochloride monohydrate.

Various tests can be carried out in animal models to show the ability of the compounds of this invention to produce blood pressure lowering action in animals and are known to correlate well with blood pressure lowering activity in humans. These are considered to be standard tests used to determine antihypertensive properties.

Determination of Antihypertensive Activity

A description of the test protocol used in the determination of the antihypertensive activity of the compounds of this invention follows:

(a) Male spontaneously hypertensive rats (SHR's) eleven weeks old, weighing 200–220 grams, are chosen for testing. The average systolic blood pressure (as measured below) should be 165 mmHg or above. Any rat not initially meeting this criterion is not utilized.

(b) A Beckman dynograph is balanced and calibrated using a Beckman indirect blood pressure coupler. A mercury manometer is placed on one arm of the glass "T" tube. The known pressure head in the tail cuff is synchronized with the recorder output so that 1 mm pen deflection=5 mmHg. Any correction is made using the chart calibration screw on the pressure coupler. The pulse amplitude is controlled by the pre-amplifier using a 20 v/cm setting.

The rats are prewarmed in groups of five for twenty minutes to dilate the tail artery from which the arterial pulse is recorded. After prewarming, each rat is placed in an individual restraining cage with continued warming. When the enclosure temperature has been maintained at 35° C. for 5 minutes, recordings are started. The tail cuff is placed at the base of the rat's tail and the rubber bulb of the pneumatic tail cuff transducer is taped securely to the ventral surface of the tail. When the rat's pulse reaches maximum amplitude and is unwavering, the cuff is inflated and the air slowly released. Systolic blood pressure is read at the point of the chart when the first pulsatile deflection appears on the chart recording while the air in the cuff is being released. The exact point of the systolic blood pressure reading is where the first deflection forms a 90° angle to the falling cuff pressure base line. After obtaining nine or ten consistent readings, the average of the middle five readings is calculated.

(c) Three groups of five to twenty rats receive the test compound at doses of 25 mg/kg p.o. A fourth group of five to twenty control rats receives distilled water. Statistical comparisons of systolic pressure (four hours after the first dose and sixteen hours after the second dose) are made on a daily basis using the Student t test for dependent variables (see, E. Lord, *Biometrika*, 34, 56 (1947), with the predose observations serving as baseline values for each rat.

Tests which show the lack of side effects of the preferred amidinourea compounds include the following:

1. Effect of Hexobarbital-Induced Loss of Righting Reflex

The test compound and a vehicle given orally thirty minutes before hexobarbital are compared for their effect on the duration of the loss of righting reflex (failure to right within five seconds) induced in groups of Swiss Webster mice (10/group, 18–20 g) by the intraperitoneal injection of hexobarbital (100 mg/kg, I.P.).

2. Effect of Plasma Glucose in Rats

Groups of 5–10 male Sprague-Dawley rats (170–210 g) are orally dosed with the test compound or the vehicle. Three hours after dosing, the rats are sacrificed by decapitation and blood is collected for plasma glucose evaluation.

3. Effect of Inducing Emesis in Dogs

Female beagle dogs (6–10 kg) are randomly selected for intravenous dosing with the test compound. Each dose of the test compounds is given to either two or four dogs. Immediately after the injection, the dogs are observed for emesis for a period of up to one hour.

In addition to the blood pressure screening, described above, certain of these compounds have undergone further studies. Utilizing standard laboratory techniques, the effect that these compounds have on blood pressure is observed following the administration of solutions containing the phenyl amidinoureas into the vertebral artery in dogs and into the lateral cerebral ventricle in rats.

In view of the results of these tests, the meta and para substituted 2,6-disubstituted phenyl amidinourea compounds of this invention possess blood pressure-lowering activity and are useful as antihypertensive agents.

The results of these tests indicate that, in general, the meta- and para- substituted phenyl amidinoureas according to this invention effect an acute reduction in blood pressure in the test subject. In addition, it has been found that the blood pressure lowering activity of compounds administered to test animals by the oral versus the parenteral route is related to the meta and para substitution on the amidinourea phenyl group.

The meta- and/or para-hydroxy 2,6-disubstituted phenyl amidinoureas and, preferably, the meta-hydroxy 2,6-disubstituted phenyl amidinoureas, exhibit good blood pressure lowering activity when administered parenterally but are less effective when administered orally in rats, for example, at doses of about 25 mg/kg or greater. In contrast, the meta-alkoxy phenylamidinoureas are preferred compounds for lowering blood pressure by oral administration. At a dose level of about 1 mg/kg in the rat, meta-methoxy 2,6-dimethyl phenylamidinourea effectively reduces blood pressure while its para-methoxy isomer is inactive. In fact, the para-methoxy compound does not exhibit a blood pressure lowering effect up to an oral dose of about 25 mg/kg.

As these tests show, the amidinoureas according to Formula I may be administered orally, parenterally or rectally. Compounds of Formula I are readily absorbed into the blood stream from the gut and are relatively nontoxic.

Table I comprises a list of blood pressure lowering compounds according to this invention. These compounds are exemplary of Applicant's invention and should not be construed as limitation thereof.

TABLE I 1-(2,6-dimethyl-4-hydroxyphenyl)-3-amidinourea
1-(2,6-dimethyl-3-hydroxyphenyl)-3-amidinourea
1-(2,6-dimethyl-3,4-dihydroxyphenyl)-3-amidinourea
1-(2,6-dimethyl-3,5-dihydroxyphenyl)-3-amidinourea
1-(2,6-dimethyl-3,4,5-trihydroxyphenyl)-3-amidinourea
1-(2,6-dichloro-4-hydroxyphenyl)-3 -amidinourea
1-(2,6-dichloro-3-hydroxyphenyl)-3-amidinourea
1-(2,6-dichloro-3,4 -dihydroxyphenyl)-3-amidinourea
1-(2,6-dichloro-3,5-dihydroxyphenyl)-3-amidinourea
1-(2,6-dichloro-3,4,5-trihydroxyphenyl)-3-amidinourea
1-(2-chloro-6-methyl-3-hydroxyphenyl)-3-amidinourea
1-(2-chloro-6-methyl-4-hydroxyphenyl)-3-amidinourea
1-(2-chloro-6-methyl-5-hydroxyphenyl)-3-amidinourea
1-(2-chloro-6-methyl-3,4-dihydroxyphenyl)-3-amidinourea
1-(2-chloro-6-methyl-3,5-dihydroxyphenyl)-3-amidinourea
1-(2-chloro-6-methyl-4,5-dihydroxyphenyl)-3-amidinourea
1-(2-chloro-6-methyl-3,4,5-trihydroxyphenyl)-3-amidinourea
1-(2,6-diethyl-4-hydroxyphenyl)-3-amidinourea
1-(2,6-diethyl-3,4-dihydroxyphenyl)-3-amidinourca
1-(2,6-diethyl-3,5-dihydroxyphenyl)-3-amidinourea
1-(2,6-dicthyl-3,4,5-trihydroxyphenyl)-3-amidinourea
1-(2,6-diethyl-3-hydroxyphenyl)-3-amidinourea
1-(2,6-dimethoxy-4-hydroxyphenyl)-3-amidinourea
1-(2,6-dimethoxy-3-hydroxyphenyl)-3-amidinourea
1-(2,6-dimethoxy-3,4-dihydroxyphenyl)-3-amidinourea
1-(2,6-dimethoxy-3,5-dihydroxyphenyl)-3-amidinourea
1-(2,6-dimethoxy-3,4,5-trihydroxyphenyl)-3-amidinourea
1-(2-chloro-6-methoxy-3-hydroxyphenyl)-3-amidinourea
1-(2-chloro-6-methoxy-4-hydroxyphenyl)-3-amidinourea
1-(2-chloro-6-methoxy-5-hydroxyphenyl)-3-amidinourea
1-(2-chloro-6-methoxy-3,4-dihydroxyphenyl)-3-amidinourea
1-(2-chloro-6-methoxy-3,5-dihydroxyphenyl)-3-amidinourea
1-(2-chloro-6-methoxy-4,5-dihydroxyphenyl)-3-amidinourea
1-(2-chloro-6-methoxy-3,4,5-trihydroxyphenyl)-3-amidinourea
1-(2,6-diethoxy-4-hydroxyphenyl)-3-amidinourea
1-(2,6-diethoxy-3,4-dihydroxyphenyl)-3-amidinourea
1-(2,6-diethoxy-3,5-dihydroxyphenyl)-3-amidinourea
1-(2,6-diethoxy-3,4,5-trihydroxyphenyl)-3-amidinourea
1-(2,6-diethoxy-3-hydroxyphenyl)-3-amidinourea
1-(2,6-dimethoxy-4-acetoxyphenyl)-3-amidinourea
1-(2,6-dimethoxy-3-methoxyphenyl)-3-amidinourea
1-(2,6-dimethoxy-3-methoxy-4-hydroxyphenyl)-3-amidinourea
1-(2,6-dimethoxy-3,5-dimethoxyphenyl)-3-amidinourea
1-(2,6-dimethoxy-3,4,5-trimethoxyphenyl)-3-amidinourea
1-(2-chloro-6-methoxy-3-methoxyphenyl)-3-amidinourea
1-(2-chloro-6-methoxy-4-benzyloxyphenyl)-3-amidinourea
1-(2-chloro-6-methoxy-5-methoxyphenyl)-3-amidinourea
1-(2-chloro-6-methoxy-3,4-methylenedioxyphenyl)-3-amidinourea
1-(2-chloro-6-methoxy-3,5-dimethoxyphenyl)-3-amidinourea
1-(2-chloro-6-methoxy-4,5-methylenedioxyphenyl)-3-amidinourea
1-(2-chloro-6-methoxy-3,4,5-trimethoxyphenyl)-3-amidinourea
1-(2,6-diethoxy-4-acetoxyphenyl)-3-amidinourea
1-(2,6-diethoxy-3-hydroxy-4-methoxyphenyl)-3-amidinourea
1-(2,6-diethoxy-3,5-dimethoxyphenyl)-3-amidinourea
1-(2,6-diethoxy-3,4,5-trimethoxyphenyl)-3-amidinourea
1-(2,6-diethoxy-3-methoxyphenyl)-3-amidinourea
1-(2,6-dimethyl-4-hydroxyphenyl)-1'-methyl-3-amidinourea
1-(2,6-dimethyl-3-hydroxyphenyl)-1'-methyl-3-amidinourea
1-(2,6-dimethyl-3,4-dihydroxyphenyl)-1'-methyl-3-amidinourea
1-(2,6-dimethyl-3,5-dihydroxyphenyl)-1'-methyl-3-amidinourea 1-(2,6-dimethyl-3,4,5-trihydroxyphenyl)-1'-methyl-3-amidinourea
1-(2,6-dichloro-4-hydroxyphenyl)-1'-methyl-3-amidinourea
1-(2,6-dichloro-3-hydroxyphenyl)-1'-methyl-3-amidinourea
1-(2,6-dichloro-3,4-dihydroxyphenyl)-1'-methyl-3-amidinourea
1-(2,6-dichloro-3,5-dihydroxyphenyl)-1'-methyl-3-amidinourea
1-(2,6-dichloro-3,4,5-trihydroxyphenyl)-1'-methyl-3-amidinourea
1-(2-chloro-6-methyl-3-hydroxyphenyl)-1'-methyl-3-amidinourea
1-(2-chloro-6-methyl-4-hydroxyphenyl)-1'-methyl-3-amidinourea
1-(2-chloro-6-methyl-3,4-dihydroxyphenyl)-1'-methyl-3-amidinourea
1-(2-chloro-6-methyl-3,5-dihydroxyphenyl)-1'-methyl-3-amidinourea
1-(2-chloro-6-methyl-4,5-dihydroxyphenyl)-1'-methyl-3-amidinourea
1-(2-chloro-6-methyl-3,4,5-trihydroxyphenyl)-1'-methyl-3-amidinourea
1-(2,6-diethyl-4-hydroxyphenyl)-1'-methyl-3-amidinourea
1-(2,6-diethyl-3,4-dihydroxyphenyl)-1'-methyl-3-amidinourea
1-(2,6-diethyl-3,5-dihydroxyphenyl)-1'-methyl-3-amidinourea
1-(2,6-diethyl-3,4,5-trihydroxyphenyl)-1'-methyl-3-amidinourea
1-(2,6-diethyl-3-hydroxyphenyl)-1'-methyl-3-amidinourea
1-(2,6-dimethyl-4-ethoxyphenyl)-3-amidinourea
1-(2,6-dimethyl-3-methoxyphenyl)-3-amidinourea
1-(2,6-dimethyl-3,4-dimethoxyphenyl)-3-amidinourea
1-(2,6-dimethyl-3-hydroxy-5-methoxyphenyl)-3-amidinourea
1-(2,6-dimethyl-3,4,5-trimethoxyphenyl)-3-amidinourea
1-(2,6-dichloro-4-benzyloxyphenyl)-3-amidinourea
1-(2,6-dichloro-3-methoxyphenyl)-3-amidinourea
1-(2,6-dichloro-3-methoxy-4-hydroxyphenyl)-3-amidinourea
1-(2,6-dichloro-3,5-dimethoxyphenyl)-3-amidinourea
1-(2,6-dichloro-3,4-methylenedioxyphenyl)-3-amidinourea
1-(2-chloro-6-methyl-3-methoxyphenyl)-3-amidinourea
1-(2-chloro-6-methyl-4-benzyloxyphenyl)-3-amidinourea
1-(2-chloro-6-methyl-5-benzyloxyphenyl)-3-amidinourea
1-(2-chloro-6-methyl-3,4-diacetoxyphenyl)-3-amidinourea
1-(2-chloro-6-methyl-3,5-dibenzyloxyphenyl)-3-amidinourea
1-(2-chloro-6-methyl-4,5-dimethoxyphenyl)-3-amidinourea
1-(2-chloro-6-methyl-3,4,5-triacetoxyphenyl)-3-amidinourea
1-(2,6-diethyl-4-acetoxyphenyl)-3-amidinourea
1-(2,6-diethyl-3-methoxy-4-hydroxyphenyl)-3-amidinourea
1-(2,6-diethyl-3,5-dibenzyloxyphenyl)-3-amidinourea
1-(2,6-diethyl-3,4,5-triacetoxyphenyl)-3-amidinourea
1-(2,6-diethyl-3-ethoxyphenyl)-3-amidinourea
1-(2,6-diethyl-3-trifluoroacetoxyphenyl)-3-amidinourea 1-(2,6-dimethyl-4-ethoxyphenyl)-1'-methyl-3-amidinourea
1-(2,6-dimethyl-3-methoxyphenyl)-1'-methyl-3-amidinourea
1-(2,6-dimethyl-3,4-dimethoxyphenyl)-1'-methyl-3-amidinourea
1-(2,6-dimethyl-3-hydroxy-5-methoxyphenyl)-1'-methyl-3-amidinourea
1-(2,6-dimethyl-3,4,5-trimethoxyphenyl)-1'-methyl-3-amidinourea
1-(2,6-dichloro-4-benzyloxyphenyl)-1'-methyl-3-amidinourea
1-(2,6-dichloro-3-methoxyphenyl)-1'-methyl-3-amidinourea
1-(2,6-dichloro-3-methoxy-4-hydroxyphenyl)-1'-methyl-3-amidinourea
1-(2,6-dichloro-3,5-dimethoxyphenyl)-1'-methyl-3-amidinourea
1-(2,6-dichloro-3,4-methylenedioxyphenyl)-1'-methyl-3-amidinourea
1-(2-chloro-6-methyl-3-methoxyphenyl)-1'-methyl-3-amidinourea
1-(2-chloro-6-methyl-4-benzyloxyphenyl)-1'-methyl-3-amidinourea
1-(2-chloro-6-methyl-5-benzyloxyphenyl)-1'-methyl-3-amidinourea
1-(2-chloro-6-methyl-3,4-diacetoxyphenyl)-1'-methyl-3-amidinourea
1-(2-chloro-6-methyl-3,5-dibenzyloxyphenyl)-1'-methyl-3-amidinourea
1-(2-chloro-6-methyl-4,5-dimethoxyphenyl)-1'-methyl-3-amidinourea
1-(2-chloro-6-methyl-3,4,5-triacetoxyphenyl)-1'-methyl-3-amidinourea
1-(2,6-diethyl-4-acetoxyphenyl)-1'-methyl-3-amidinourea
1-(2,6-diethyl-3-methoxy-4-hydroxyphenyl)-1'-methyl-3-amidinourea
1-(2,6-diethyl-3,5-dibenzyloxyphenyl)-1'-methyl-3-amidinourea
1-(2,6-diethyl-3,4,5-triacetoxyphenyl)-1'-methyl-3-amidinourea
1-(2,6-diethyl-3-ethoxyphenyl)-1'-methyl-3-amidinourea
1-(2,6-diethyl-3-trifluroracetoxyphenyl)-1'-3-amidinourea In general, the dosage regimen in carrying out the method of this invention is that which insures maximum therapeutic response until improvement is obtained, and thereafter, the minimum effective level which gives relief. Generally, the daily dose for adults will be between about 5 and about 50 mg/day total dose (preferably about 30 mg/day administered in 2 or 3 equal doses at about 8 to 12 hour intervals), bearing in mind, of course, that in selecting the appropriate dosage in any specific case, consideration must be given to the patient's weight, general health, age and other factors which may influence response to the drug.

The dosage amounts used in administering the drug, parenterally or by any other route, can be adjusted as necessary to provide and maintain effective blood pressure levels, for example, when the drug is administered directly by intravenous infusion, the rate of infusion can be adjusted to provide blood levels equivalent to those achieved through oral administration. Generally, the drug will be administered orally, though in situations such as malignant hypertension or other emergency situations, i.v. or other forms of administration may be used.

Further, the active amidinourea may be administered alone or in admixture with other agents having the same or different pharmacological properties. For example, an active amidinourea according to Formula I may be formulated into a pharmaceutical composition containing an amidinourea which exhibits a slow acting (multiple dose dependent) blood pressure lowering effect. The administration of this composition to a patient is effective in inducing a relatively quick and a time dependent delayed blood pressure reduction. The slow acting amidinourea could be the 2,6-disubstituted phenyl N-alkyl amidinourea (wherein the meta and para positions in the phenyl group are unsubstituted) according to the invention disclosed and claimed in copending U.S. application Ser. No. 26,161, noted above. The administration of the combined formulation may be by oral, intravenous or other route. The oral therapy preferably uses a combined formulation containing a 3-alkoxy-phenyl-amidinourea while the intravenous therapy uses a combined formulation containing a 3- or 4-hydroxyphenylamidinourea.

Although the optimum quantities for administration of the compounds of Formula I in accordance with the present invention will depend on the compound employed and the particular type of condition treated, oral dose levels of preferred compounds, when administered to humans in total daily doses of about 0.01 to about 5 mg/per kg of body weight, given separately, are particularly useful. The preferred dose range is about 0.1 to about 2/mg/kg/day.

Orally these compounds may be administered in tablets, hard or soft capsules, aqueous or oily suspensions, dispersible powders or granules, emulsions, syrups or elixirs. The optimum dosage, of course, will depend on the particular compound being used and the type and severity of the condition being treated.

In the preferred form, the compounds of this invention are prepared for oral administration in either tablet or capsule form, depending upon the solubility and capability of the specific amidinourea chosen and the other ingredients.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc., in order to provide a pharmaceutically appealing and palatable preparation. The compositions may contain selected excipients, for example: inert diluents such as calcium carbonate, lactose, etc.; guanulating and disintegrating agents such as magnesium stearate, etc.; binding such as starch gelatin, etc.; suspending agents such as methylcellulose, vegetable oil, etc.; dispersing agents such as lecithin, etc.; thickening agents such as beeswax, hard parafin, etc.; emulsifying agents such as naturally occurring gums, etc.; non-irritating excipients such as cocoa butter, polyethylene glycols, etc.; and the like. Further, in formulating these compounds, for every 100 parts by weight of the composition, there may be present between about 5 and about 95 parts by weight of the active ingredient. The dosage unit form will generally contain between about 0.1 mg and about 50 mg of the active ingredient of this invention. The preferred unit dose is between about 5 mg and about 15 mg.

The following examples illustrate the preparation of tablets and capsules which constitute the preferred dosage forms for oral administration of the compounds of Formula I in accordance with the method of this invention and sterile solutions for parenteral administration:

EXAMPLE IV

A batch of homogenous tablets is prepared, each having the following formula:

| Per Tablet | Ingredients | Per 1,000 Tablets |
| --- | --- | --- |
| 5 mg | 1-(2',6'-dimethyl-3-methoxyphenyl)-3-amidinourea hydrochloride | 5 gm |
| 100 mg | Microcrystalline cellulose | 100 gm |
| 150 mg | Cornstarch | 150 gm |
| 450 mg | Deionized water | 450 gm |
| 10 mg | Hydrogenated castor oil | 10 gm |
| 715 mg | | 715 gm |

The following procedure is used to prepare the tablets. 1-(2',6'-dimethyl-3-methoxyphenyl)-3-amidinourea, cellulose and 100 gm of starch are blended together dry. A paste of the remaining starch is prepared with deionized water in a steam-jacketed pot. The two components are mixed, guanulated and passed through a #8 screen, then dried in a fluid bed dryer at about 40° C. and again passed through a #14 mesh screen. The composition is then formed into tablets by compressing on a Stokes Rotary Multi-Layer Tablet Press.

EXAMPLE V

A lot of two-piece hard gelatin capsules, each containing 5 mg of 1-(2',6'-dimethyl-3-methoxyphenyl)-3-amidinourea is prepared from the following types and amounts of ingredients (the amounts given are per capsule):

| 1-(2',6'-dimethyl-3-methoxyphenyl)-3-amidinourea hydrochloride | 5 g |
| --- | --- |
| dicalcium phosphate | 500 g |
| talc | 150 g |
| magnesium stearate | 5 g |

The ingredients are mixed thoroughly and filled into capsules which are used for oral administration at the rate of about one every four hours. If desired, slow release forms can be provided or delayed release forms, depending on choice of capsules and formulating ingredients.

By analogous methods and employing techniques known to the art, there are prepared formulations suitable for administration of an effective amount of any of the amidinoureas of Formula I.

EXAMPLE VI 50 g of 1-(2',6'-dimethyl-3-hydroxyphenyl)-3-amidinourea hydrochloride, 5 g of propyl p-hydroxybenzoate are dissolved and diluted to 5000 cc with twice-distilled water after the addition of modified Sorenson buffer solution in an amount sufficient to adjust the pH value to a pH of 6.0. Sodium chloride is dissolved therein in an amount sufficient to render the resulting solution isotonic. The final solution is passed through a bacteriological filter and the filtrate is autoclaved at 120° C. for 15 minutes to yield a parenterally applicable solution which contains 50 mg of 1-(2',6'-dimethyl-3-hydroxyphenyl)-3-amidinourea hydrochloride in 5 cc.

We claim:

1. A compound according to the formula:

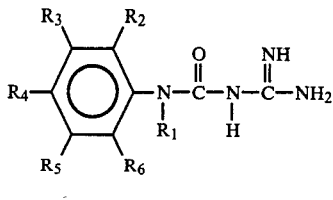

wherein:

$R_1$ is hydrogen or lower alkyl;

$R_2$ and $R_6$ may be the same or different and are lower alkyl, halo, lower alkoxy, nitro, halo lower alkyl, or lower alkylsulfonyl;

$R_3$, $R_4$ and $R_5$ may be the same or different and are hydrogen, hydroxy, lower alkoxy, phenyl or substituted phenyl lower alkoxy, lower alkenyloxy, lower alkynyloxy, halo lower alkyl acyloxy, or lower alkyl acyloxy;

provided that at least one of $R_3$ and $R_5$ is other than hydrogen; and $R_3$ and $R_4$ together may be carbonyldioxy, methylenedionxy or ethylenedioxy and form a 5 or 6 membered heterocyclic ring;

and wherein substituted phenyl in which one or more phenyl hydrogens are replaced by halo, lower alkyl, halo lower alkyl, nitro, amino, lower alkanoyl, hydroxy, lower alkoxy, phenyl lower alkoxy, cyano, halo lower alkoxy, and lower alkyl sulfonyl;

or a non-toxic pharmaceutically acceptable salt thereof.

2. A compound according to claim 1 wherein $R_4$ is hydrogen, hydroxy, phenyl lower alkoxy or lower alkyl acyloxy.

3. A compound according to claim 1 wherein $R_4$ and at least one of $R_3$ and $R_5$ is hydroxy, lower alkoxy, phenyl lower alkoxy, or lower alkyl acyloxy.

4. A method for lowering blood pressure in mammalian species comprising administering to a patient, an effective blood pressure lowering amount of a compound of the formula

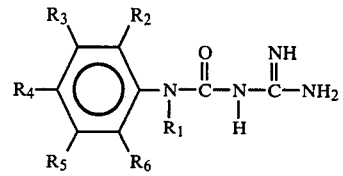

wherein:

$R_1$ is hydrogen or lower alkyl;

$R_2$ and $R_6$ may be the same or different and are lower alkyl, halo, lower alkoxy, nitro, halo lower alkyl, or lower alkylsulfonyl;

$R_3$, $R_4$, and $R_5$ may be the same or different and are hydrogen, hydroxy, lower alkoxy, phenyl or substituted phenyl lower alkoxy, lower alkenyloxy, lower alkynyloxy, halo lower alkyl acyloxy, or lower alkyl acyloxy;

provided that at least one of $R_3$ and $R_5$ is other than hydrogen; and $R_3$ and $R_4$ together may be carbonyldioxy, methylenedioxy or ethylenedioxy and form a 5 or 6 membered heterocyclic ring;

and wherein substituted phenyl means phenyl in which one or more phenyl hydrogens are replaced by halo, lower alkyl, halo lower alkyl, nitro, amino, lower alkanoyl, hydroxy, lower alkoxy, phenyl lower alkoxy, cyano, halo lower alkoxy, and lower alkyl sulfonyl;

or a non-toxic pharmaceutically acceptable salt thereof.

5. A pharmaceutical composition comprising an effective blood pressure lowering amount of a compound according to claim 1 and a pharmaceutically acceptable carrier.

* * * * *